United States Patent
Fisk et al.

(10) Patent No.: US 10,487,385 B2
(45) Date of Patent: Nov. 26, 2019

(54) TITANIUM BASED CERAMIC REINFORCED ALLOY

(71) Applicant: Pulse Technologies, Inc., Quakertown, PA (US)

(72) Inventors: Andrew E. Fisk, Philadelphia, PA (US); Anatolii Demchyshyn, Kiev (UA); Leonid Kulak, Kiev (UA); Mykola Kuzmenko, Kiev (UA)

(73) Assignee: Pulse IP, LLC, Quakertown, PA (US)

( * ) Notice: Subject to any disclaimer, the term of this patent is extended or adjusted under 35 U.S.C. 154(b) by 221 days.

(21) Appl. No.: 15/652,095

(22) Filed: Jul. 17, 2017

(65) Prior Publication Data

US 2018/0016669 A1    Jan. 18, 2018

Related U.S. Application Data

(60) Provisional application No. 62/363,497, filed on Jul. 18, 2016.

(51) Int. Cl.
| | |
|---|---|
| *C22F 1/18* | (2006.01) |
| *A61L 31/02* | (2006.01) |
| *B22D 7/00* | (2006.01) |
| *B22D 21/00* | (2006.01) |
| *C22C 14/00* | (2006.01) |

(52) U.S. Cl.
CPC ............ *C22F 1/183* (2013.01); *A61L 31/022* (2013.01); *B22D 7/005* (2013.01); *B22D 21/005* (2013.01); *C22C 14/00* (2013.01)

(58) Field of Classification Search
CPC ................... C22C 14/00; C22F 1/183
See application file for complete search history.

(56) References Cited

FOREIGN PATENT DOCUMENTS

RU    2211254 C2 *   8/2003   ............ C22C 14/00

OTHER PUBLICATIONS

English Abstract and English Machine Translation of Sysoeva (RU 2211254) (Aug. 11, 2003).*

* cited by examiner

*Primary Examiner* — Jessee R Roe
(74) *Attorney, Agent, or Firm* — Massina Pat. & TM Law PLLC

(57) ABSTRACT

A titanium based, ceramic reinforced body formed from an alloy having from about 3 wt. % to about 10 wt. % of zirconium, about 10 wt. % to about 25 wt. % of niobium, from about 0.5 wt. % to about 2 wt. % of silicon, and from about 63 wt. % to about 86.5 wt. % of titanium. The alloy has a hexagonal crystal lattice α phase of from about 20 vol % to about 70 vol %, and a cubic body centered β crystal lattice phase of from about 30 vol. % to about 80 vol. %. The body has an ultimate tensile strength of about 950 MPa or more, and a Young's modulus of about 150 GPa or less. A molten substantially uniform admixture of a zirconium, niobium, silicon, and titanium alloy is formed, cast into a shape, and cooled into body. The body may then be formed into a desired shape, for example, a medical implant and optionally annealed.

18 Claims, No Drawings

TITANIUM BASED CERAMIC REINFORCED ALLOY

This application claims the benefit of U.S. Provisional Application Ser. No. 62/363,497, filed on Jul. 18, 2016, the contents of which are incorporated herein by reference.

BACKGROUND OF THE INVENTION

Field of the Invention

The invention relates to a titanium based, ceramic reinforced alloy. More particularly, the invention pertains to a ceramic reinforced alloy comprising titanium, niobium, zirconium and silicon. The alloy has both an α crystal phase and a β crystal phase. The alloy has an ultimate tensile strength of about 950 MPa or more, and elongation of more than 6%, and a Young's modulus of about 150 GPa or less. In one application, the alloy is for use in producing medical implants.

Description of the Related Art

There is great commercial interest in the production of biocompatible, medically suitable implants for surgically jointing bone and implanting teeth. Medical implants such as screws, pins, rods, bars, springs, coils, cables, staples, clips, plates and the like require materials with very high tensile strength and high cyclic fatigue life while also having a modulus of elasticity low enough to be compatible with bone. Common alloys include titanium, stainless steel and cobalt chrome alloys. Stainless steel and cobalt chrome alloys exhibit very high tensile strength, but both contain nickel and chromium which are known irritants to the body. In addition, these alloys have low ductility and a Young's modulus approaching five times that of bone. This high tensile strength and Young's modulus also makes it difficult to machine these components cost effectively using conventional techniques. Titanium and its alloys are especially popular choices for orthopedic bone screws and plates commonly used for spinal fixation.

Titanium alloys for a variety of applications are known in the art and there are numerous literature references disclosing a wide range of elements which are used to provide alloys having desired characteristics, such as increased tensile strength and ductility. Generally, titanium and its alloys may exist in one or a mixture of two basic crystalline structures, namely the α phase, which is a hexagonal close-packed structure, and the β phase which is a body-centered cubic structure. The commercially pure grades of titanium alloys have low tensile strengths but show no signs of tissue irritation. These alloys are commonly used for orthopedic plates which are implanted externally to the bone structure and can therefore have a larger size. $Ti_6AlV_4$ alloys are commonly used for higher strength applications such as fixation screws or plates which must be contained in a small area. One known medically implantable alloy is disclosed in U.S. Pat. No. 6,752,882. It provides a biocompatible low modulus, high strength titanium-niobium alloy containing a phase as a major phase and consisting essentially of 10-30 wt % of Nb and the balance titanium. U.S. Pat. No. 5,954,724 relates to titanium alloys suitable for use for medical implants and devices having a high-strength, low-modulus, and high hardness with improved corrosion resistance due to the addition of hafnium and molybdenum, and which additionally allow for surface hardening of an implant made of this alloy. U.S. Pat. No. 7,892,369 provides a method for modifying the microstructure of titanium alloys for use in the manufacture of orthopedic prostheses. An orthopedic prosthesis is initially formed from a titanium alloy and subsequently subjected to a thermal treatment followed by rapid quenching. The microstructure of the titanium alloy in the prosthesis has improved resistance to fretting fatigue. U.S. Pat. No. 7,682,473 provides an implant prosthesis composed of a TiAlNb alloy having a modulus near that for bone to prevent stress shielding, and a tensile and compressive strength and fracture toughness equal to or greater than that of bone. A key problem with other alloys which use aluminum and vanadium is the suspected effect of Al and V when movement and fretting are involved. The release of Al and V into the blood stream could cause irritation for the patient in the long term. Another issue with certain grades of titanium is the so called "notch effect" during cyclic fatigue. Prepared and polished samples of certain titanium alloys have been shown to have fatigue strength near the ultimate tensile strength. However, when a notch is introduced to the sample, the fatigue strength can be lowered to 40% of the ultimate tensile strength. Since implantable devices must be laser marked with the appropriate tracking information, a notch situation always exists and care must be taken not to exceed the notch fatigue strength.

The problems associated with designing an implantable device are specifically, providing an alloy with high tensile strength, and a marginal Young's modulus that contains no known irritants which can be economically machined with conventional methods. The present invention addresses all these issues.

SUMMARY OF THE INVENTION

The invention provides an alloy of titanium, zirconium, niobium and silicon. Titanium and niobium alloys are known to form alloys with very low Young's modulus (50-80 GPa). A problem with these known alloys is that they do not have sufficient strength for the manufacture of orthopedic devices such as bone plates and fixation screws. This invention overcomes the limitations of conventional alloys by including within a solid solution of the metals, a glassy silicon ceramic which acts to absorb energy during crack propagation and retard dislocations during applied stress. The atomic percent of this glassy silicon ceramic is controlled as to still allow for a moderately low Young's modulus and good formability.

U.S. Pat. No. 9,039,963, which is incorporated herein by reference and commonly owned with the present application, teaches of a tertiary alloy of Ti—Nb—Si having similar mechanical properties gained through the creation of specific alpha and beta lattice phases. This balance of phases must be accomplished through heat treatments during processing and homogeneous properties can be difficult achieve. The present invention achieves similar mechanical properties by providing a chemical composition which stabilizes the formation of silicide in the system.

The invention provides a body comprising an alloy, the alloy comprising from about 3 wt. % to about 10 wt. % zirconium, from about 10 wt. % to about 25 wt. % of niobium, from about 0.5 wt. % to about 2 wt. % of silicon, and the balance being titanium, the alloy having a hexagonal crystal lattice α phase of from about 20 vol % to about 70 vol %, and a cubic body centered β crystal lattice phase of from about 30 vol. % to about 80 vol. %. The body has an ultimate tensile strength of about 950 MPa or more, and a Young's modulus of about 150 GPa or less. The inventors have identified the benefit of formation of silicide particles within the crystal matrix of the alloy. The silicide particles act as strengthening agents to the alloy which accounts for its mechanical properties being better than alloys of the prior art.

The invention also provides a method of forming a body which comprises forming a molten alloy comprising a substantially uniform admixture of from about 3 wt. % to about 10 wt. % zirconium, from about 10 wt. % to about 25 wt. % of niobium, from about 0.5 wt. % to about 2 wt. % of silicon, and the balance being titanium, casting the molten alloy into a shape, and then cooling the shape into the body, the alloy having a hexagonal crystal lattice α phase of from about 20 vol % to about 70 vol %, and a cubic body centered β crystal lattice phase of from about 30 vol. % to about 80 vol. %, the body having an ultimate tensile strength of about 950 MPa or more, and a Young's modulus of about 150 GPa or less. The alloy also comprises a metallic constituent of Ti—Nb—Z in some form of metal solution and a second constituent of ceramic silicides such as $(TiZr)_5Si_3$, $(TiZr)_3Si$ and similar. The presence of the silicides, their size and distribution achieves an advantageous structure over the prior art alloys. The addition of the Nb to the Ti alloy has the effect of decreasing the Young's Modulus to the desired range but it in turn lowers the tensile strength of the alloy making the system unfit for use. The addition of Si increases that tensile strength so long as the silicides are uniformly distributed about the grains but the elongation is decreased as the size of the silicides increased. This increase is often due to heating of the alloy to a high temperature to promote the uniform distribution of silicides. The addition of Zr to the Ti—Nb—Si alloy acts to reduce the size of the silicides by the formation of complex $(TiZr)_5Si_3$, $(TiZr)_3Si$ and similar ceramic constituent. It is desirable to have an elongation greater than 4% and preferably between 6% and 15% so that implant does not fail in a brittle manner during use and to allow for ease of machining and other mechanical forming processes. This allows an alloy to be formed having the optimal properties for a medical implant. The process of forming the alloy and subsequently tempering the alloy in its final or intermediate state is beneficial to the resulting structure. The heating and cooling of the alloy forms and distributes the silicide particles such that the desired mechanical properties are achieved.

DETAILED DESCRIPTION OF THE INVENTION

An alloy is formed by combining commercially pure quantities of titanium, zirconium, niobium and silicon. These may be obtained in the form of bars, wires, powders, particles, or any other convenient form. These are then heated until each is molten and blended into a substantially uniform admixture. The amount of zirconium may range from about 3 wt. % to about 10 wt. %. The amount of niobium may range from about 10 wt. % to about 25 wt. %. The amount of silicon may range from about 0.5 wt. % to about 2 wt. %. Preferably the alloy has no more than 2 wt. % of nitrogen, oxygen, or carbon. The balance of the alloy is titanium. In a most preferred embodiment, the alloy comprises only these four elements such that the alloy has from about 3 wt. % to about 10 wt. % of zirconium, from about 10 wt. % to about 25 wt. % of niobium, from about 0.5 wt. % to about 2 wt. % of silicon, and the balance being titanium, apart from incidental impurities.

A method for preparing such a high strength, low modulus, biocompatible titanium alloy involves mechanically blending the above components, and then heating them until melted, one or more times.

The alloys are preferably made by mechanically blending accurately weighed portions of the pure elements and melting the blend in a furnace such as a plasma arc furnace or vacuum arc furnace, and remelting as necessary to achieve uniformity, and then casting and cooling. One example of a method of melting includes combining the components in a commercially available arc-melting vacuum pressure casting system. A melting chamber is first evacuated and purged with an inert gas such as argon. An argon pressure of, for example 1.5 $kgf/cm^2$ may be maintained during melting. The appropriate amounts of titanium, zirconium, niobium and silicon are prepared by electron beam skull melting with induction stirring of the melt. The resulting mixture may optionally be re-melted multiple times to improve homogeneity. In one embodiment, the molten alloy is then cast, or drawn out of the crucible by a water cooled rod to form a cylindrical ingot, with cooling.

Generally, the molten alloy is cast into a body in the form of an ingot, however, it is recognized that the molten alloy may be cast directly into a desired shape. When cast as an ingot, the resulting ingot may then be formed directly into the desired medial implant shape, such as those in the form of a screw, pin, rod, bar, spring, coil, cable, staple, clip, plate, or the like. More typically the ingot is made into an intermediate shape such as a rod, bar, sheet or plate which can then be mechanically formed into customized shapes such as those conforming to hip joint stems, femoral heads, knee femoral components, knee tibial components, intramedullary nails, inner ear vent tubes, spinal plates, spinal disks, pelvic plates, dental implants, cardiovascular implants, compression hip screws, and the like. Such forming may be done by the use of customary machine tooling. The cast ingot, intermediate shape or the machined medical implant may be annealed to form and distribute the complex silicide constituents in order to meet the optimal properties. Annealing may be done by heating at temperatures ranging from about 950° C. to about 1200° C. for from about 20 minutes to about 90 minutes followed by a rapid cooling/quenching. After forming the alloy into the desired shape, the alloy may be polished, anodized or treated by other well-known methods to impart other desirable properties. Polishing may be done by mechanical burnishing. Anodizing may be done by electrochemically oxidizing the surface.

The alloy and the body made from the alloy has a combination crystal lattice structure of both α and β phases with a ceramic constituent of mainly complex silicides. In particular, the alloy has a hexagonal crystal lattice α phase of from about 20 vol % to about 70 vol %, and a cubic body centered β crystal lattice phase of from about 30 vol. % to about 80 vol. % with a structure of small and complex silicide evenly distributed about the grains.

The following non-limiting examples serve to illustrate the invention.

EXAMPLES

Three alloys were formed and tested in both the as cast condition, and after annealing in vacuum. The alloys were prepared by electron beam skull melting with induction stirring of the melt. The resulting material was drawing out of the crucible by a water cooled rod to form a cylindrical ingot.

| Alloy Test | Condition | Nb | Zr | Si | UTS (Mpa) | Young's Modulus (GPa) | Yield Strength (Mpa) | Elongation (%) | Temperature (C.) | Time (min) |
|---|---|---|---|---|---|---|---|---|---|---|
| 1  | As Cast  | 12 | 6 | 1 | 1060 | N/A | 950  | 4.6 | | |
| 2  | As Cast  | 19 | 6 | 1 | 910  | N/A | 800  | 8   | | |
| 1a | Annealed | 12 | 6 | 1 | 1145 | 85  | 840  | 12  | 1050 | 60 |
| 2a | Annealed | 19 | 6 | 1 | 950  | N/A | 670  | 13  | 1050 | 30 |
| 2b | Annealed | 19 | 6 | 1 | 1075 | 92  | 1100 | 9   | 1150 | 60 |
| 2c | Annealed | 19 | 6 | 1 | 1170 | 88  | 820  | 13  | 1100 | 60 |

The sample ingots were subjected to machinability tests, polishing tests and color anodizing. The composition performed excellently in all cases, with the polishing and anodizing exceeding the characteristics of commercially available Grade 4 and Grade 23 titanium.

While the alloy is described with reference to use for a medical implant, the invention is not limited to such and the alloy may be utilized for other applications requiring materials with very high tensile strength and high cyclic fatigue life while also having a relatively low modulus of elasticity.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as defined in the claims.

What is claimed is:

1. A body comprising an alloy, the alloy comprising from about 3 wt. % to about 10 wt. % of zirconium, about 10 wt. % to about 25 wt. % of niobium, from about 0.5 wt. % to about 2 wt. % of silicon, and from about 63 wt. % to about 86.5 wt. % of titanium, the alloy having a hexagonal crystal lattice α phase of from about 20 vol % to about 70 vol %, and a cubic body centered β crystal lattice phase of from about 30 vol. % to about 80 vol. %, the body having an ultimate tensile strength of about 950 MPa or more, and a Young's modulus of about 150 GPa or less.

2. The body of claim 1 wherein the alloy comprises from about 3 wt. % to about 10 wt. % of zirconium, about 10 wt. % to about 25 wt. % of niobium, from about 0.5 wt. % to about 2 wt. % of silicon, and the balance titanium.

3. The body of claim 1 which has an ultimate tensile strength of from about 1000 MPa to about 1400 MPa, and a Young's modulus of from about 100 GPa to about 150 GPa.

4. The body of claim 1 which has an ultimate tensile strength of from about 1100 MPa to about 1300 MPa, and a Young's modulus of from about 110 GPa to about 140 GPa.

5. The body of claim 1 wherein the alloy has no more than 2 wt. % of nitrogen, no more than 2 wt. % of oxygen, and no more than 2 wt. % of carbon.

6. The body of claim 1 wherein the alloy has about 1 wt. % of nitrogen or less, about 1 wt. % of oxygen or less, and about 1 wt. % of carbon or less.

7. The body of claim 1 wherein the alloy has about 0.5 wt. % of nitrogen or less, about 0.5 wt. % of oxygen or less, and about 0.5 wt. % of carbon or less.

8. The body of claim 1 wherein the alloy comprises a hexagonal crystal lattice α phase of from about 40 vol. % to about 70 vol. %, and a cubic body centered β crystal lattice phase of from about 30 vol. % to about 60 vol. %.

9. The body of claim 1 wherein the alloy comprises a hexagonal crystal lattice α phase of from about 45 vol. % to about 65 vol. %, and a cubic body centered β crystal lattice phase of from about 45 vol. % to about 60 vol. %.

10. A medical implant formed from the body of claim 1.

11. The medical implant of claim 10 which is in the form of a screw, pin, rod, bar, spring, coil, cable, staple, clip or plate.

12. A method of forming a body which comprises forming a molten alloy comprising a substantially uniform admixture of from about 3 wt. % to about 10 wt. % of zirconium, about 10 wt. % to about 25 wt. % of niobium, from about 0.5 wt. % to about 2 wt. % of silicon, and from about 63 wt. % to about 86.5 wt. % of titanium, casting the molten alloy into a shape, and then cooling the shape into the body, the alloy having a hexagonal crystal lattice α phase of from about 20 vol % to about 70 vol %, and a cubic body centered β crystal lattice phase of from about 30 vol. % to about 80 vol. %, the body having an ultimate tensile strength of about 950 MPa or more, and a Young's modulus of about 150 GPa or less.

13. The method of claim 12 wherein the alloy comprises from about 3 wt. % to about 10 wt. % of zirconium, about 10 wt. % to about 25 wt. % of niobium, from about 0.5 wt. % to about 2 wt. % of silicon, and the balance being titanium.

14. The method of claim 12 further comprising the subsequent step of forming the body into a medical implant.

15. The method of claim 14 wherein the medical implant is in the form of a screw, pin, rod, bar, spring, coil, cable, staple, clip or plate.

16. The method of claim 14 further comprising the subsequent step of annealing the medical implant.

17. The method of claim 12 further comprising the subsequent step of annealing the body.

18. The method of claim 12 wherein the alloy has no more than 2 wt. % of nitrogen, no more than 2 wt. % of oxygen, and no more than 2 wt. % of carbon.

* * * * *